US 11,096,833 B2

(12) United States Patent
Hudson

(10) Patent No.: US 11,096,833 B2
(45) Date of Patent: Aug. 24, 2021

(54) METHOD AND APPARATUS FOR DRYING INKS PRINTED ON HEAT SENSITIVE ABSORBENT ARTICLE COMPONENTS

(71) Applicant: The Procter & Gamble Company, Cincinnati, OH (US)

(72) Inventor: Kasey Marie Hudson, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/699,852

(22) Filed: Dec. 2, 2019

(65) Prior Publication Data

US 2020/0100948 A1    Apr. 2, 2020

Related U.S. Application Data

(62) Division of application No. 15/980,786, filed on May 16, 2018, now Pat. No. 10,524,961.

(Continued)

(51) Int. Cl.
*A61F 13/15* (2006.01)
*B41M 7/00* (2006.01)
(Continued)

(52) U.S. Cl.
CPC .. *A61F 13/15577* (2013.01); *A61F 13/15731* (2013.01); *A61F 13/47* (2013.01);
(Continued)

(58) Field of Classification Search
CPC .......... A61F 13/15577; A61F 13/15731; A61F 13/84; A61F 13/47; A61F 13/51394;
(Continued)

(56) References Cited

U.S. PATENT DOCUMENTS 2,075,189 A    3/1937 Galligan et al.
3,025,199 A    3/1962 Harwood
(Continued)

FOREIGN PATENT DOCUMENTS

AR    92853-0001    3/2018
CN    1315168 A    10/2001
(Continued)

OTHER PUBLICATIONS

PCT International Search Report, dated Jul. 20, 2018, 15 pages.
(Continued)

*Primary Examiner* — Huan H Tran
*Assistant Examiner* — Alexander D Shenderov
(74) *Attorney, Agent, or Firm* — Jay A. Krebs

(57) ABSTRACT

The present disclosure relates to methods and apparatuses for printing and drying inks on substrates. Printing systems may include a metering device positioned between a printing station and a light source. During operation, the printing station deposits ink onto a substrate to define a printed region. And the light source directs infrared light onto the substrate to define an illumination zone. The printed region is advanced from the printing station to the metering device and from the metering device through the illumination zone, wherein the ink is dried with infrared light traveling from the light source, which also heats the substrate and changes the modulus of elasticity of the substrate. In turn, the metering device isolates the printing station from the change in the modulus of elasticity to help reduce phase shifts caused by changes in the modulus of elasticity resulting from heat in the substrate.

7 Claims, 5 Drawing Sheets

Related U.S. Application Data

(60) Provisional application No. 62/507,253, filed on May 17, 2017.

(51) Int. Cl.

| | |
|---|---|
| *B41J 11/00* | (2006.01) |
| *B65H 20/10* | (2006.01) |
| *B65H 37/00* | (2006.01) |
| *B41M 3/00* | (2006.01) |
| *A61F 13/84* | (2006.01) |
| *A61F 13/47* | (2006.01) |
| *A61F 13/513* | (2006.01) |
| *B41F 23/00* | (2006.01) |
| *B41F 17/00* | (2006.01) |
| *B41M 5/00* | (2006.01) |
| *B41J 15/04* | (2006.01) |

(52) U.S. Cl.
CPC ........ *A61F 13/51394* (2013.01); *A61F 13/84* (2013.01); *B41F 17/006* (2013.01); *B41F 23/005* (2013.01); *B41J 11/002* (2013.01); *B41J 11/0085* (2013.01); *B41J 15/048* (2013.01); *B41M 3/00* (2013.01); *B41M 5/0011* (2013.01); *B41M 5/0047* (2013.01); *B41M 5/0064* (2013.01); *B41M 7/009* (2013.01); *B65H 20/10* (2013.01); *B65H 37/00* (2013.01); *A61F 2013/15715* (2013.01); *A61F 2013/15829* (2013.01); *A61F 2013/8497* (2013.01); *B65H 2301/517* (2013.01)

(58) Field of Classification Search
CPC .... A61F 2013/15715; A61F 2013/8497; A61F 2013/15829; B41F 23/005; B41F 17/006; B41M 5/0011; B41M 5/0047; B41M 5/0064; B41M 7/009; B41M 3/00; B41J 15/048; B41J 11/0085; B41J 11/002; B65H 20/10; B65H 37/00; B65H 2301/517
USPC ........................................................ 347/102
See application file for complete search history.

(56) References Cited

U.S. PATENT DOCUMENTS

| | | | |
|---|---|---|---|
| 3,465,350 A | 9/1969 | Keur et al. |
| 3,465,351 A | 9/1969 | Keur et al. |
| 3,848,594 A | 11/1974 | Buell |
| 3,860,003 A | 1/1975 | Buell |
| 4,033,263 A | 7/1977 | Richmond |
| 4,107,364 A | 8/1978 | Sisson |
| 4,209,563 A | 6/1980 | Sisson |
| 4,321,924 A | 3/1982 | Ahr |
| 4,425,130 A | 1/1984 | DesMarias |
| 4,515,595 A | 5/1985 | Kievit et al. |
| 4,589,876 A | 5/1986 | Van Tilburg |
| 4,610,678 A | 9/1986 | Weisman et al. |
| 4,662,875 A | 5/1987 | Hirotsu et al. |
| 4,673,402 A | 6/1987 | Weisman et al. |
| 4,695,278 A | 9/1987 | Lawson |
| 4,704,115 A | 11/1987 | Buell |
| 4,795,454 A | 1/1989 | Dragoo |
| 4,834,735 A | 5/1989 | Alemany et al. |
| 4,834,741 A | 5/1989 | Sabee |
| 4,846,815 A | 7/1989 | Scripps |
| 4,888,231 A | 12/1989 | Angstadt |
| 4,894,060 A | 1/1990 | Nestegard |
| 4,909,803 A | 3/1990 | Aziz et al. |
| 4,940,464 A | 7/1990 | Van Gompel et al. |
| 4,946,527 A | 8/1990 | Battrell |
| 4,950,264 A | 8/1990 | Osborn, III |
| 5,151,092 A | 2/1992 | Buell et al. |
| 5,092,861 A | 3/1992 | Nomura et al. |
| 5,167,897 A | 12/1992 | Weber et al. |
| 5,221,274 A | 6/1993 | Buell et al. |
| 5,246,433 A | 9/1993 | Hasse et al. |
| 5,286,543 A | 2/1994 | Ungpiyakul et al. |
| 5,330,458 A | 7/1994 | Buell et al. |
| 5,359,525 A | 10/1994 | Weyenberh |
| 5,360,420 A | 11/1994 | Cook et al. |
| 5,401,268 A | 3/1995 | Rodier |
| 5,562,646 A | 10/1996 | Goldman et al. |
| 5,569,234 A | 10/1996 | Buell et al. |
| 5,599,335 A | 2/1997 | Goldman et al. |
| 5,628,097 A | 5/1997 | Benson et al. |
| 5,643,588 A | 7/1997 | Roe et al. |
| 5,669,894 A | 9/1997 | Goldman et al. |
| 5,674,216 A | 10/1997 | Buell et al. |
| 5,702,551 A | 12/1997 | Huber et al. |
| 5,735,840 A | 4/1998 | Kline et al. |
| 5,897,545 A | 4/1999 | Kline et al. |
| 5,916,661 A | 6/1999 | Benson et al. |
| 5,928,212 A | 7/1999 | Kline et al. |
| 5,957,908 A | 9/1999 | Kline et al. |
| 5,968,025 A | 10/1999 | Roe et al. |
| 6,107,537 A | 8/2000 | Elder et al. |
| 6,107,539 A | 8/2000 | Palumbo et al. |
| 6,118,041 A | 9/2000 | Roe et al. |
| 6,120,487 A | 9/2000 | Ashton |
| 6,120,489 A | 9/2000 | Johnson et al. |
| 6,153,209 A | 11/2000 | Vega et al. |
| 6,200,297 B1 | 3/2001 | Boulanger |
| 6,234,605 B1 | 5/2001 | Hilton |
| 6,251,097 B1 | 6/2001 | Kline et al. |
| 6,309,052 B1 | 10/2001 | Prasad et al. |
| 6,410,129 B2 | 6/2002 | Zhang et al. |
| 6,426,444 B2 | 7/2002 | Roe et al. |
| 6,432,098 B1 | 8/2002 | Kline et al. |
| 6,464,316 B1 | 10/2002 | Askeland et al. |
| 6,471,430 B1 * | 10/2002 | Gaus ......................... B41J 3/60 271/276 |
| 6,546,197 B2 | 4/2003 | Muller et al. |
| 6,547,354 B1 | 4/2003 | Askeland et al. |
| 6,586,652 B1 | 7/2003 | Roe et al. |
| 6,617,016 B2 | 9/2003 | Zhang et al. |
| 6,627,787 B1 | 9/2003 | Roe et al. |
| 6,669,618 B2 | 12/2003 | Reising et al. |
| 6,689,112 B1 | 2/2004 | Blanchard |
| 6,783,519 B2 | 8/2004 | Samuelsson |
| 6,790,798 B1 | 9/2004 | Suzuki et al. |
| 6,801,828 B2 | 10/2004 | Popp et al. |
| 6,811,239 B1 | 11/2004 | Salacz |
| 6,820,022 B2 | 11/2004 | Popp et al. |
| 6,825,393 B2 | 11/2004 | Roe et al. |
| 6,861,571 B1 | 3/2005 | Roe et al. |
| 6,932,802 B2 | 3/2005 | Luizzi, Jr. |
| 6,957,884 B2 | 10/2005 | Sharma et al. |
| 7,123,981 B2 | 10/2006 | Dollevoet et al. |
| 8,137,721 B2 | 3/2012 | Wen et al. |
| 8,145,343 B2 | 3/2012 | DeBruler et al. |
| 8,145,344 B2 | 3/2012 | DeBruler et al. |
| 8,217,095 B2 | 7/2012 | Yamaguchi et al. |
| 8,244,393 B2 | 8/2012 | McLaughlin et al. |
| 8,273,066 B2 | 9/2012 | Anderson et al. |
| 8,349,916 B2 | 1/2013 | Kawashima et al. |
| 8,986,273 B2 | 3/2015 | Mercer et al. |
| 9,006,509 B2 | 4/2015 | Anderson et al. |
| 9,211,356 B2 | 12/2015 | Gruenbacher et al. |
| 9,238,740 B2 | 1/2016 | Baptista et al. |
| 9,944,073 B2 | 4/2018 | Strasemeier et al. |
| 2001/0015746 A1 | 8/2001 | Yosimura et al. |
| 2002/0165512 A1 | 11/2002 | Drevik |
| 2003/0233082 A1 | 12/2003 | Kline et al. |
| 2004/0097895 A1 | 5/2004 | Busam et al. |
| 2004/0138636 A1 | 7/2004 | Cardin et al. |
| 2004/0158212 A1 | 8/2004 | Ponomarenko et al. |
| 2004/0201660 A1 | 10/2004 | Nishikawa et al. |
| 2004/0243087 A1 | 12/2004 | Kinoshita et al. |
| 2004/0258886 A1 | 12/2004 | Maclag |
| 2005/0015066 A1 | 1/2005 | Anderson et al. |
| 2005/0124959 A1 | 6/2005 | Alcantara et al. |

(56) References Cited

U.S. PATENT DOCUMENTS

| | | |
|---|---|---|
| 2005/0283131 A1 | 12/2005 | Zander et al. |
| 2006/0033764 A1 | 2/2006 | Aoki |
| 2006/0081151 A1 | 4/2006 | Raksha et al. |
| 2006/0116652 A1 | 6/2006 | Miura et al. |
| 2006/0142710 A1 | 6/2006 | Kigata |
| 2007/0062785 A1* | 3/2007 | Werner ............... B41F 23/0443 198/780 |
| 2007/0078427 A1 | 4/2007 | Raycheck et al. |
| 2007/0093769 A1 | 4/2007 | Kline et al. |
| 2007/0100309 A1 | 5/2007 | Uda |
| 2007/0126831 A1 | 6/2007 | Suzuki et al. |
| 2007/0273739 A1 | 11/2007 | Rodin |
| 2007/0289484 A1 | 12/2007 | Yamaguchi et al. |
| 2008/0015536 A1 | 1/2008 | Digiacomantonio |
| 2008/0091156 A1 | 4/2008 | Maldonado et al. |
| 2009/0312730 A1 | 12/2009 | LaVon et al. |
| 2010/0064917 A1 | 3/2010 | Blanchard et al. |
| 2010/0233446 A1 | 9/2010 | Kawashima et al. |
| 2010/0312215 A1 | 12/2010 | Odoi |
| 2011/0247508 A1 | 10/2011 | Baptista et al. |
| 2012/0133716 A1 | 5/2012 | Aizawa et al. |
| 2012/0222576 A1 | 9/2012 | McNeil et al. |
| 2012/0249630 A1 | 10/2012 | Bugner et al. |
| 2013/0072887 A1 | 3/2013 | LaVon et al. |
| 2013/0123731 A1 | 5/2013 | Mercer |
| 2013/0211356 A1 | 8/2013 | Nishikawa et al. |
| 2013/0284946 A1 | 10/2013 | Schaede |
| 2013/0306226 A1 | 11/2013 | Zink et al. |
| 2013/0335473 A1* | 12/2013 | Ramesh .................... B41J 2/21 347/15 |
| 2014/0015887 A1 | 1/2014 | Seccombe |
| 2014/0184681 A1 | 7/2014 | Itogawa |
| 2014/0288520 A1 | 9/2014 | Kuramochi |
| 2014/0296420 A1 | 10/2014 | Baptista et al. |
| 2014/0343525 A1 | 11/2014 | Roh et al. |
| 2015/0015649 A1 | 1/2015 | Warner et al. |
| 2015/0057632 A1 | 2/2015 | Luzader et al. |
| 2016/0038353 A1 | 2/2016 | Bonilla et al. |
| 2016/0235607 A1 | 8/2016 | Mercer et al. |
| 2017/0081533 A1* | 3/2017 | Brust ................... C09D 11/322 |
| 2017/0354549 A1 | 12/2017 | Cho |
| 2018/0032575 A1 | 11/2018 | Vohwinkel |
| 2018/0325750 A1 | 11/2018 | Vohwinkel |
| 2018/0325753 A1 | 11/2018 | Vohwinkel |
| 2018/0325754 A1 | 11/2018 | Vohwinkel |
| 2018/0333307 A1 | 11/2018 | Hudson |
| 2019/0290506 A1 | 9/2019 | Kuramochi |

FOREIGN PATENT DOCUMENTS

| | | |
|---|---|---|
| DE | 202010002859 | 5/2010 |
| EP | 1208823 A1 | 5/2002 |
| EP | 1293186 A3 | 9/2004 |
| EP | 1528907 B1 | 9/2008 |
| EP | 3075365 A1 | 10/2016 |
| EP | 3505148 B1 | 5/2020 |
| FR | 883712 A | 7/1943 |
| GB | 2142874 A | 1/1985 |
| JP | 2003339764 A | 12/2003 |
| JP | 2013009892 A | 1/2013 |
| JP | 2013220225 A | 10/2013 |
| JP | 2014223218 A | 12/2014 |
| WO | 2010110270 A1 | 9/2010 |
| WO | 2019008090 A1 | 1/2019 |

OTHER PUBLICATIONS

All Office Actions, U.S. Appl. No. 15/980,786.
All Office Actions, U.S. Appl. No. 15/976,946.
All Office Actions. U.S. Appl. No. 15/977,025.
All Office Actions, U.S. Appl. No. 15/977,047.
All Office Actions, U.S. Appl. No. 15/976,901.
All Office Actions; U.S. Appl. No. 17/341,730.
U.S. Unpublished U.S. Appl. No. 17/341,730, filed Jun. 8, 2021, to Henning Vohwinkel et al.

* cited by examiner

METHOD AND APPARATUS FOR DRYING INKS PRINTED ON HEAT SENSITIVE ABSORBENT ARTICLE COMPONENTS

CROSS REFERENCE TO RELATED APPLICATIONS

This application is a divisional of U.S. application Ser. No. 15/980,786, filed on May 16, 2018, which claims the benefit of U.S. Provisional Application No. 62/507,253, filed on May 17, 2017, both of which are incorporated by reference herein.

FIELD OF THE INVENTION

The present disclosure relates to apparatuses and methods for printing absorbent article component substrates, and more particularly, methods and apparatuses for drying inks printed on heat sensitive substrates.

BACKGROUND OF THE INVENTION

Along an assembly line, various types of disposable absorbent articles, such as diapers and sanitary napkins, may be assembled by adding components to and otherwise modifying advancing, continuous webs of material. Webs of material and component parts used to manufacture diapers may include: backsheets, topsheets, absorbent cores, front and/or back ears, fastener components, and various types of elastic webs and components such as leg elastics, barrier leg cuff elastics, and waist elastics. Webs of material and component parts used to manufacture sanitary napkins may include: backsheets, topsheets, secondary topsheets, absorbent core components, release paper wrappers, and the like. In some configurations, graphics are printed on individual components and/or continuous webs of material used to assemble the absorbent articles. The graphics may be provided by printing ink on substrate materials by various printing methods, such as flexographic printing, rotogravure printing, screen-printing, inkjet printing, and the like.

In some configurations, printing operations are performed separate to the assembly process, such as for example, printing the substrates offline wherein the printed substrates may be stored until needed for production. For example, printing operations may be accomplished on discrete printing lines, separately from converting lines that are dedicated to manufacturing disposable absorbent articles. After printing on the printing lines, the printed substrates are delivered to the converting lines, such as in a form of continuous webs comprising printed images thereon. In addition to or alternatively to offline printing, graphic printing may be done online during the article assembly process.

Some current printing operations may utilize solvent and/or aqueous based inks to print graphics. However, solvent and/or aqueous based inks may require additional processing steps after the ink is printed. Such additional process steps may include drying operations that may require evaporation of some ingredient of the inks, such as a solvent or a thinner. External heating systems may also be required to complete these drying steps. As such, the required drying steps may be difficult to complete at relatively high manufacturing and/or printing speeds to ensure printed inks are adequately dried before subjecting printed substrates to additional processing operations. During the drying process, a light source such as infrared light may be used to impart energy to the ink to evaporate a solvent. And the energy imparted to the ink from the light source is proportional to the intensity of the light directed at the ink and the time during which ink is subjected to the light. The amount of energy required to dry an ink will vary based on a number of different factors. For example, for an ink deposited in a particular area of a substrate, the amount of energy required to dry the ink deposited in that area will increase or decrease along with the amount of ink deposited in that area. Thus, the intensity of the light and/or the time at which the ink is subjected to the intensity may be increased or decreased depending on the amount of ink in a particular area.

Some of the light used to dry the ink may also be absorbed by the substrate and converted into heat energy. As such, drying ink printed on heat sensitive substrates, such as nonwovens and films, may present various challenges. For example, in some configurations where printing is performed online during an article assembly process, a printed substrate may be required to advance past the light source at a relatively high rate of speed. As such, the time during which printed ink is exposed to light may be relatively short. As discussed above, in order to dry the ink in a relatively short period of time, the intensity of the light may need to be increased to relatively high levels. However, if the intensity of the light is too high over a period of time, the heat energy created in the substrate by the light may destroy and/or damage the advancing substrate. In some instances, a light source may be configured to heat an advancing substrate web to a temperature that is below a softening point of the substrate material. However, even though the light source may not heat the substrate enough to damage the substrate, enough heat may be imparted to the substrate to change the modulus of elasticity of the substrate. In turn, the change in the modulus of elasticity of the substrate may result in a phase shift during the printing operation, wherein some ink is applied to the substrate in undesired locations. Such phase shifts may be readily noticeable in printed regions, and in turn, may detract from aesthetically pleasing aspects of the printed regions.

Consequently, there remains a need to configure ink printing systems to help ensure that ink printed on a substrate can be dried at relatively high speeds without damaging the substrate and/or causing undesired phase shifts in printing operations caused by changes in the modulus of elasticity of the substrate.

SUMMARY OF THE INVENTION

In one aspect, a method for printing comprises the steps of: providing a substrate extending in a machine direction, the substrate comprising a first surface and an opposing second surface and defining a width in a cross direction; directing infrared light from a light source onto the first surface of the substrate to define an illumination zone on the first surface of the substrate; advancing the substrate under a printing station; ejecting ink from the printing station onto the first surface of the substrate to define a printed region; advancing the substrate and the printed region from the printing station to a metering device; advancing the printed region from the metering device through the illumination zone; drying the ink advancing through the illumination zone with infrared light traveling from the light source.

In another aspect, a method for printing comprises the steps of: providing a substrate extending in a machine direction, the substrate comprising a first surface and an opposing second surface and defining a width in a cross direction; directing infrared light from a light source onto the first surface of the substrate to define an illumination zone extending for a length, L (m), in the machine direction on the first surface of the substrate; advancing the substrate under a printhead; ejecting ink from the printhead onto the first surface of the substrate to define a printed region; advancing the substrate and the printed region from the printhead to a vacuum conveyor; advancing the printed region from the vacuum conveyor through the illumination zone; drying the ink advancing through the illumination zone with infrared light traveling from the light source.

In yet another aspect, an apparatus for printing a substrate extending in a machine direction and comprising a first surface and an opposing second surface and defining a width in a cross direction, the apparatus comprises: a supply of water based ink; a printing station positioned to deposit ink from the supply onto the first surface of the substrate; an ink dryer comprising a light source positioned to direct infrared light toward the first surface of the substrate at a location downstream in the machine direction from the printing station, wherein heat from the ink dryer causes changes in the modulus of elasticity of the substrate; and a means for eliminating phase shifting caused by changes in the modulus of elasticity of the substrate, the means for eliminating phase shifting is positioned between the printing station and the ink dryer.

DETAILED DESCRIPTION OF THE INVENTION

Figure 1:
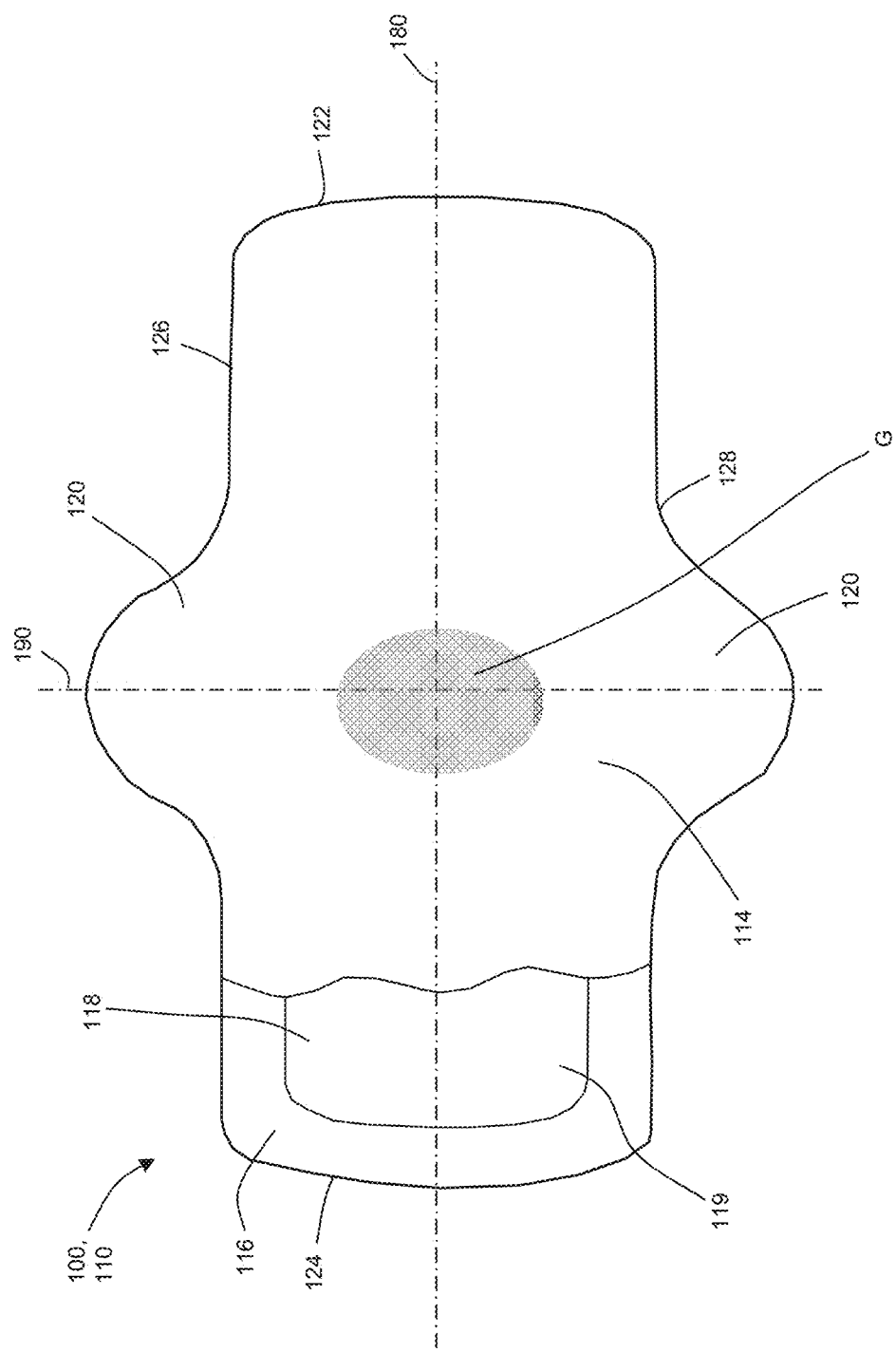
FIG. 1 is a plan view of an absorbent article.

The following term explanations may be useful in understanding the present disclosure: "Absorbent article" is used herein to refer to consumer products whose primary function is to absorb and retain soils and wastes. Absorbent articles can comprise sanitary napkins, tampons, panty liners, interlabial devices, wound dressings, wipes, disposable diapers including taped diapers and diaper pants, inserts for diapers with a reusable outer cover, adult incontinent diapers, adult incontinent pads, and adult incontinent pants. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "infrared light" refers herein to light having wavelengths of about 700 nm to about 1 mm.

The term "modulus" and "modulus of elasticity" refers herein to a tensile modulus or Young's Modulus of a substrate and may be defined by a ratio of stress (force per unit area) along an axis to strain (ratio of deformation over an initial length) along the axis.

The term "nonwoven" refers herein to a material made from continuous (long) filaments (fibers) and/or discontinuous (short) filaments (fibers) by processes such as spunbonding, meltblowing, carding, and the like. In some configurations, a nonwoven may comprise a polyolefin based nonwoven, including but not limited to nonwovens having polypropylene fibers and/or polyethylene fibers and/or bicomponent fibers comprising a polyolefin. Nonlimiting examples of suitable fibers include spunbond, spunlaid, meltblown, spunmelt, solvent-spun, electrospun, carded, film fibrillated, melt-film fibrillated, air-laid, dry-laid, wet-laid staple fibers, and other nonwoven web materials formed in part or in whole of polymer fibers as known in the art, and workable combinations thereof. Nonwovens do not have a woven or knitted filament pattern. It is to be appreciated that nonwovens having various basis weights can be used in accordance with the methods herein. For example, some nonwovens may have a basis weight of at least about 8 gsm, 12 gsm, 16 gsm, 20 gsm, 25 gsm, 25 gsm, 40 gsm, or 65 gsm. Some nonwovens may have basis weight of about 8 gsm to about 65 gsm, specifically reciting all 1 gsm increments within the above-recited ranges and all ranges formed therein or thereby.

It is to be appreciated that films having various basis weights can be used in accordance with the methods herein. For example, some films may have a basis weight of at least about 8 gsm, 12 gsm, 16 gsm, 20 gsm, 25 gsm, 25 gsm, 40 gsm, or 60 gsm. Some films may have basis weight of about 8 gsm to about 60 gsm, specifically reciting all 1 gsm increments within the above-recited ranges and all ranges formed therein or thereby.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

Aspects of the present disclosure relate to methods and apparatuses for printing absorbent article substrates, and in particular, methods and apparatuses for printing and drying inks printed on substrates. The substrate extends in a machine direction MD, defines a width in a cross direction CD, and includes a first surface and an opposing second surface. As discussed in more detail below, printing systems according to the present disclosure may include a metering device positioned between a printing station and a light source. During operation, the printing station deposits ink onto the first surface of the substrate to define a printed region. And the light source directs infrared light onto the first surface of the substrate to define an illumination zone extending for a length in the machine direction on the first surface of the substrate. The substrate is advanced in the machine direction to advance the printed region from the printing station to the metering device and from the metering device through the illumination zone. As the printed region advances through the illumination zone, the ink is dried with infrared light traveling from the light source. While the printed region advances through the illumination zone at a speed, the infrared light also heats the substrate, which in turn, changes the modulus of elasticity of the substrate. However, the metering device isolates the printing station from the change in the modulus of elasticity to help reduce or eliminate phase shifts due to changes in the modulus of elasticity of the substrate caused by heat in the substrate from the infrared light. Maintaining a relatively constant substrate modulus of elasticity at the printing station helps to provide color to color registration by helping to maintain a relatively constant substrate unit length at the printing station while under tension. The substrate also has an onset temperature $T_{onset}$ (C°). While the printed region advances through the illumination zone at a speed, the infrared light heats the substrate from an initial temperature $T_{in}$ (C°) entering the illumination zone to a maximum temperature $T_{max}$ (C°), wherein $T_{max}$ (C°)≤$T_{onset}$ (C°). As such, the printing systems herein may be configured and operated to help ensure that the ink is dried at relatively high speeds without damaging the substrate by overheating the substrate.

It is to be appreciated that the systems and methods disclosed herein are applicable to work with various types of converting processes and/or machines, such as for example, absorbent article manufacturing, packaging, and/or printing processes. For the purposes of a specific illustration, FIG. 1 shows an example of an absorbent article 100 that may be printed in accordance with the methods and apparatuses disclosed herein. In particular, FIG. 1 shows one example of a plan view of an absorbent article 100 configured as a sanitary napkin 110. The sanitary napkin 110 may comprise a liquid permeable topsheet 114, a liquid impermeable, or substantially liquid impermeable, backsheet 116, and an absorbent core 118. The liquid impermeable backsheet 116 may or may not be vapor permeable. The absorbent core 118 may have any or all of the features described herein with respect to the absorbent core 118 and, in some forms, may have a secondary topsheet 119 (STS) instead of acquisition materials. The STS 119 may comprise one or more channels. In some forms, channels in the STS 119 may be aligned with channels in the absorbent core 118. The sanitary napkin 110 may also comprise wings 120 extending outwardly with respect to a longitudinal axis 180 of the sanitary napkin 110. The sanitary napkin 110 may also comprise a lateral axis 190. The wings 120 may be joined to the topsheet 114, the backsheet 116, and/or the absorbent core 118. The sanitary napkin 110 may also comprise a front edge 122, a back edge 124 longitudinally opposing the front edge 122, a first side edge 126, and a second side edge 128 longitudinally opposing the first side edge 126. The longitudinal axis 180 may extend from a midpoint of the front edge 122 to a midpoint of the back edge 124. The lateral axis 190 may extend from a midpoint of the first side edge 126 to a midpoint of the second side edge 128. The sanitary napkin 110 may also be provided with additional features commonly found in sanitary napkins as is known in the art.

With regard to the sanitary napkin 110 of FIG. 1, the secondary topsheet 119 incorporating fluid etched stratum of heterogeneous mass may be bonded to, or otherwise attached to the topsheet 114. In some embodiments, thermal point calendaring or other suitable bonding is utilized. In other embodiments, the fluid etched stratum of heterogeneous mass may serve as an absorbent core of an absorbent article. The fluid etched stratum of heterogeneous mass may serve as the topsheet for an absorbent article, the secondary topsheet of an absorbent article. Additionally, an absorbent article may utilize two or more fluid etched stratums of heterogeneous masses within one absorbent article. For example, panty liners and incontinence pads may be formed with the fluid etched stratum of heterogeneous mass positioned between a topsheet and a bottom sheet to function as an absorbent core. Furthermore the fluid etched absorbent structure having a first layer and a second layer may not include a binder component.

The sanitary napkin 110 may have any shape known in the art for feminine hygiene articles, including the generally symmetric "hourglass" shape, as well as pear shapes, bicycle-seat shapes, trapezoidal shapes, wedge shapes or other shapes that have one end wider than the other.

The topsheet 114, the backsheet 116, and the absorbent core 118 may be assembled in a variety of well-known configurations, including so called "tube" products or side flap products, such as, for example, configurations are described generally in U.S. Pat. Nos. 4,950,264; 4,425,130; 4,321,924; and 4,589,876, all of which are incorporated by reference herein.

As previously mentioned, absorbent articles may be assembled with various components that may be printed off-line, before assembly, or on-line, as part of the assembly process. As such, the absorbent articles herein may include graphics printed on various components. Thus, in the context of the previous discussion, the apparatuses and methods herein may be used to print substrates configured as continuous substrates and/or discrete components of an absorbent article 100, either off-line or on-line. For example, the apparatuses and methods herein may be utilized in to print graphics on any of the topsheet 114; backsheet 116; secondary topsheet 119; and/or absorbent core 118. For example, the secondary topsheet 114 of the sanitary napkin 110 shown in FIG. 1 includes graphics G that may be printed before, during, and/or after assembly. As discussed in more detail below, the systems and methods herein may be utilized to print such graphics before, during, and/or after assembly. Although the apparatuses and methods are described herein in the context of the feminine hygiene article 110, such as shown in FIG. 1, it is to be appreciated that the methods and apparatuses herein may be used to print various substrates that can be used with various process configurations and/or absorbent articles, such as for example, taped diapers and diaper pants.

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674, 216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1, all of which are incorporated by reference herein.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 5,246,433; 5,569,234; 6,120,487; 6,120,489; 4,940,464; 5,092,861; 5,897,545; 5,957,908; and U.S. Patent Publication No. 2003/0233082, all of which are incorporated by reference herein.

Figure 2:
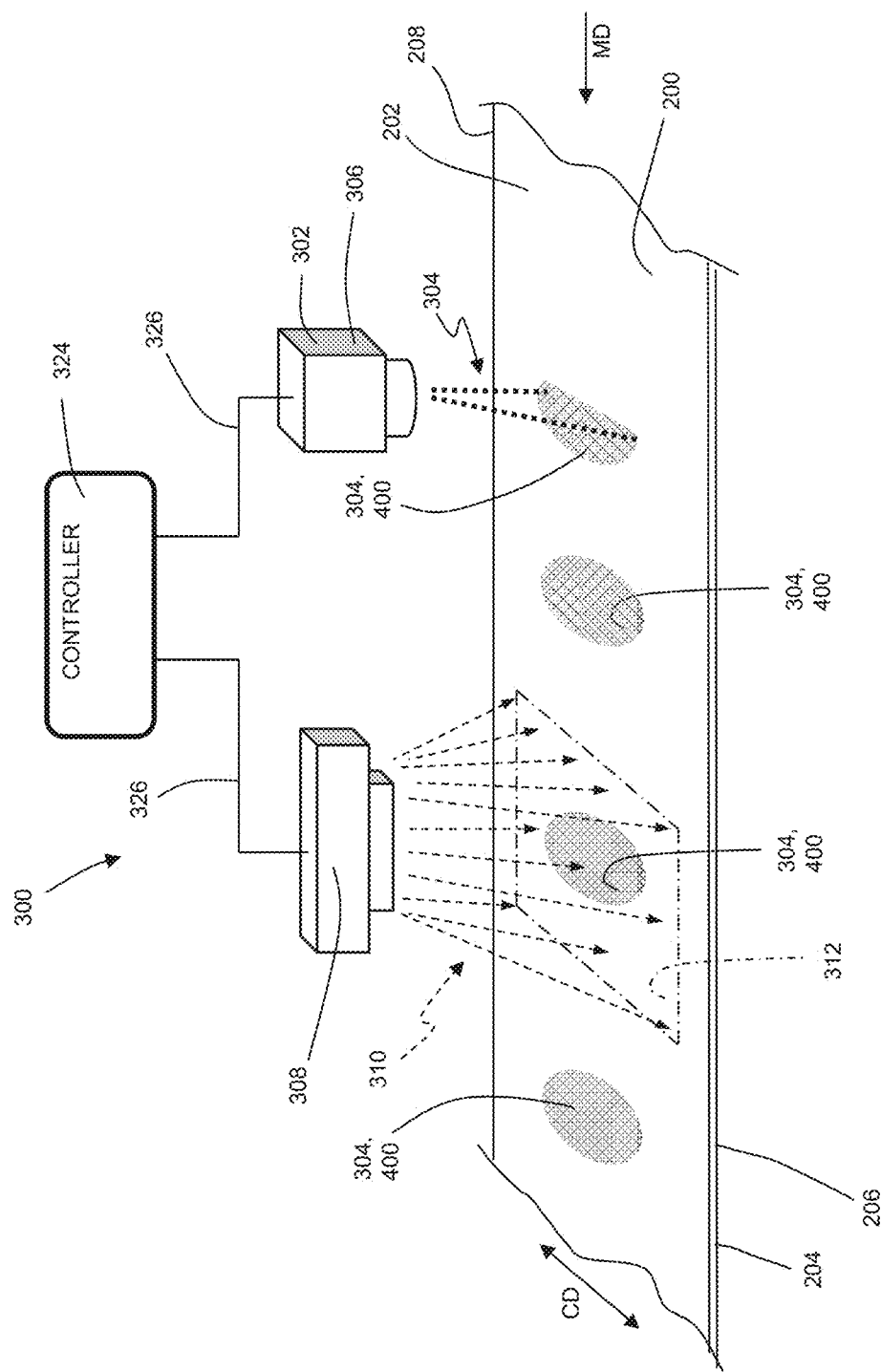
FIG. 2 is a schematic side view of a printing system for printing an advancing substrate.

It is to be appreciated that the printing systems and methods disclosed herein are applicable to work with various types of converting processes and/or machines. For example, FIG. 2 shows a schematic representation of a converting process including a printing apparatus or system 300 for printing graphics on a substrate 200 advancing in a machine direction MD. The substrate 200 may be a continuous substrate and may include a first surface 202 and an opposing second surface 204. The substrate 200 may also define a width Ws extending in the cross direction CD between a first longitudinal side edge 206 and a second longitudinal side edge 208.

Figure 3:
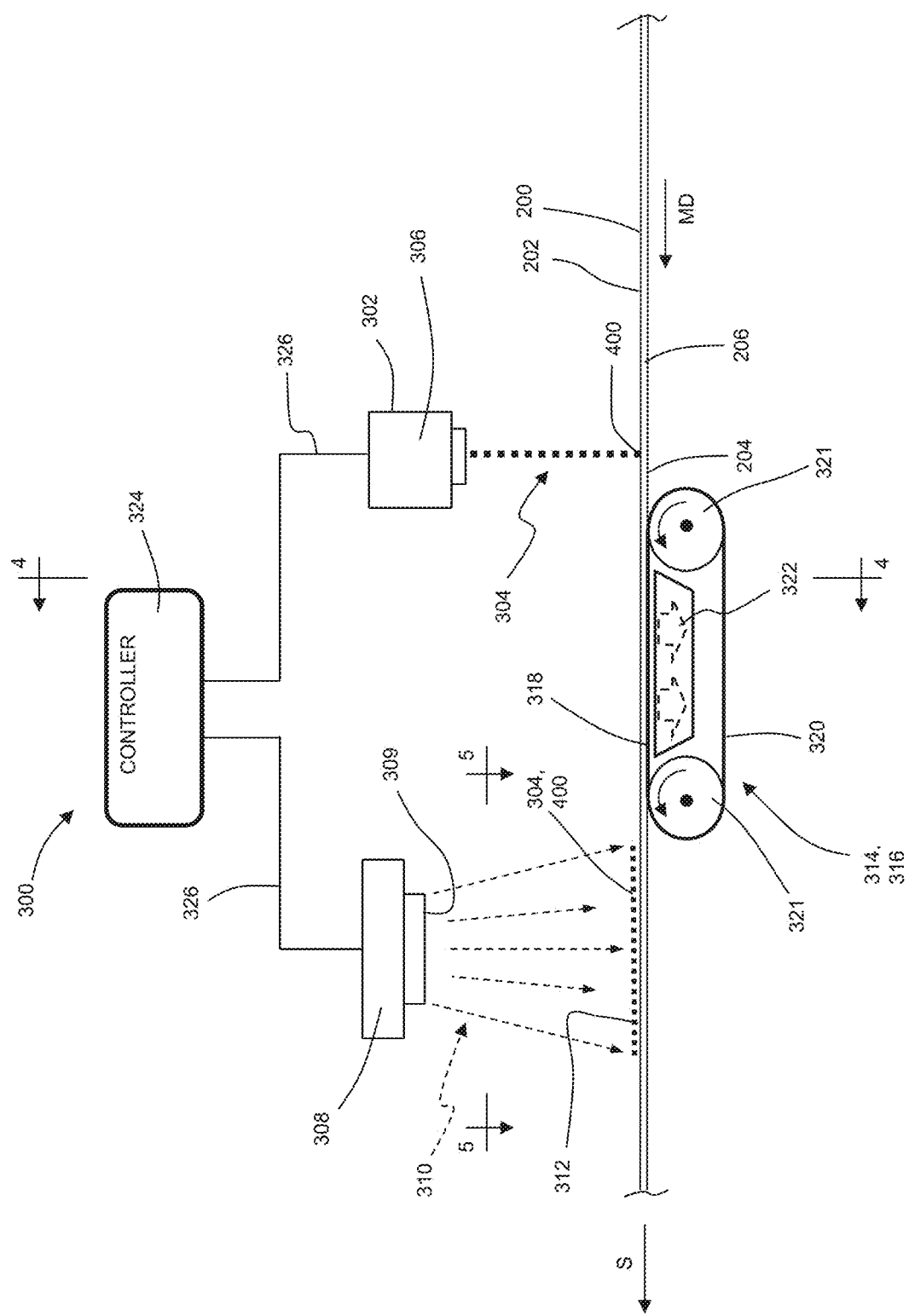
FIG. 3 is a left side view of the substrate and printing system of FIG. 2 showing a metering device positioned between a printing station and a light source.
Figure 4:
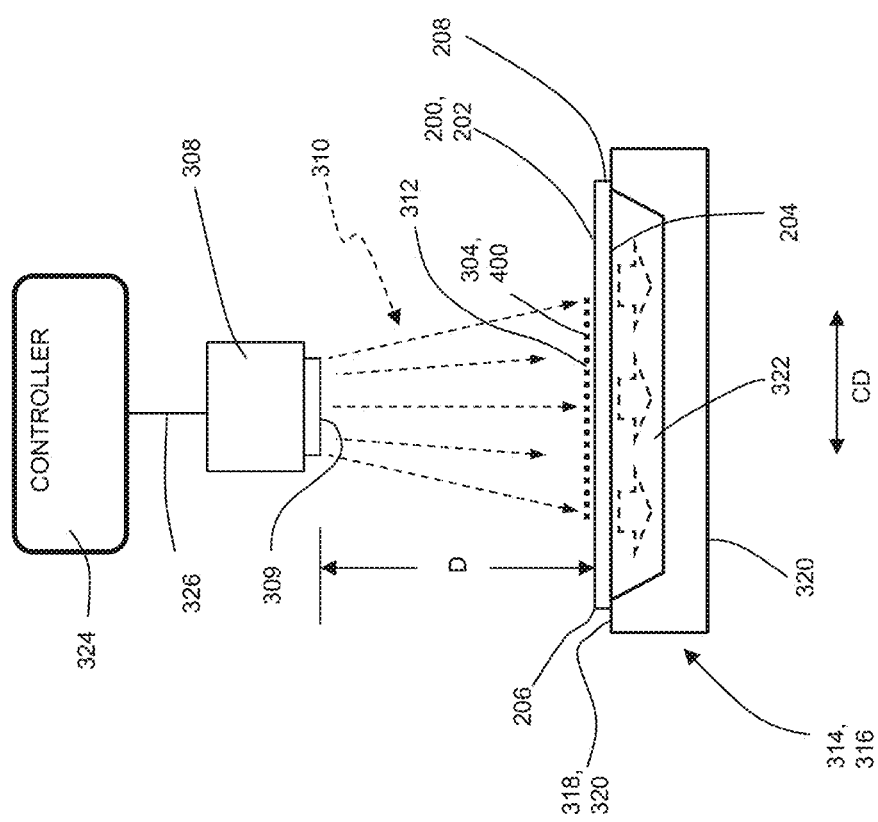
FIG. 4 is a cross sectional view of the substrate and printing system along the sectional line 4-4 of FIG. 3.

As shown in FIGS. 2-4, the printing system 300 may include a printing station 302. During operation, the substrate 200 advances in the machine direction MD a speed, S (m/s). In turn, the printing station 302 deposits ink 304 onto the first surface 202 of the advancing substrate 200 to define a printed region 400. It is to be appreciated that the advancing substrate 200 may be supported in various ways to mitigate movement while ink 304 is being deposited and/or dried on the substrate 200. For example, the second surface 204 of the substrate 200 may be supported by a conveyor having a series of rollers, an advancing belt, and/or a rotating drum. It is to be appreciated that the printed substrate 200 may be subjected to additional manufacturing operations, such as combining and/or cutting operations, during assembly of a product.

It is to be appreciated that the substrates 200 herein may be advanced in the machine direction MD at various speeds S. For example, the substrate 200 may be configured to advance in the machine direction MD at a speed S of about 0.5 meters/second (m/s) to about 15 m/s, specifically reciting all 1 m/s increments within the above-recited ranges and all ranges formed therein or thereby. In some configurations, the speed S is equal to or greater than about 6 m/s to about 10 m/s. As shown in FIG. 2, the printing system 300 also includes a light source 308 that directs infrared light 310 onto the first surface 202 of the substrate 200 to define an illumination zone 312 extending in the machine direction MD on the first surface 202. The printed region 400 advances through the illumination zone 312. In turn, ink 304 advancing through the illumination zone 312 is dried with the infrared light 310 traveling from the light source 308.

As discussed above, the infrared light 310 from the light source 308 applies heat energy to the ink 304 in the illumination zone 312. In turn, the heat causes some ingredients of the ink 304, such as a solvent, water, or thinner, to evaporate, which dries the ink 304. Heat energy from the infrared light 310 is also absorbed by the substrate 200, which in turn, changes the modulus of elasticity of the substrate 200. As such, the printing 300 may also include a metering device 314 positioned between the printing station 302 and the light source 308. In particular, the metering device 314 contacts and advances the substrate 200 downstream of where of the ink 304 is deposited thereon and upstream of the illumination zone 312. As such, during operation, the substrate 200 and the printed region 400 advance in the machine direction MD from the printing station 302 to the metering device 314. And from the metering device 314, the substrate 200 and the printed region 400 advance in the machine direction MD to the illumination zone 312. Because the substrate advances from the printing station 302 directly to the metering device 314 before proceeding to the illumination zone 312, the metering device 314 helps to prevent undesired phase shifting in the printing operation that might otherwise occur as a result of changes the modulus of elasticity of the substrate 200.

As shown in FIGS. 3 and 4, the metering device 314 may be configured as a conveyor 316 including a carrier surface 318 that contacts and advances the substrate 200 in the machine direction. The conveyor 316 may include a belt 320 routed in an endless loop around two or more rollers 321. In addition, the carrier surface 318 may be configured as a porous and/or apertured belt or other foraminous carrier surface in fluid communication with a vacuum system 322. As such, suction forces from the vacuum system 322 may be exerted on the substrate 200 to hold the substrate 200 on the carrier surface 318. In some configurations, the metering device may be configured with other or additional mechanisms and/or systems to attract and/or hold substrate 200 on the carrier surface 318, such as for example, static electricity discharge bars and/or adhesive. In some configurations, the carrier surface 318 may configured with various different surface textures to increase frictional forces between the carrier surface 318 and the first and/or second surfaces 202, 204 of the substrate 200. In some configurations, metering device 314 may include a pneumatic system including nozzles that direct pressurized air toward the carrier surface 318. As such, pressurized air may be directed toward the first surface 202 of the substrate 200 to help push the second surface 204 of the substrate 200 against the carrier surface 318.

It is to be appreciated that the metering device 314 may be configured in various ways. For example, the metering device 314 may be configured to include additional belt conveyors that may be positioned to contact opposing surfaces 202, 204 of the substrate 200 to create nips extending along the machine direction MD. In some configurations, the metering device 314 may be configured as a rotating drum with an outer circumferential surface that defines the carrier surface 318. In some configurations, the metering device 314 may include two or more rollers position adjacent each other to define a nip through which the substrate 200 advances.

It is also to be appreciated that the substrate 200 may be configured in various ways. For example, the substrate 200 herein may be configured as a single nonwoven substrate or a single film substrate that defines both the first surface 202 and the second surface 204. It is also to be appreciated that the substrate 200 herein may be configured as a laminate including various layers of substrates bonded together, wherein a nonwoven substrate layer defines the first surface 202 and another substrate layer defines the second surface 204. For example, the substrate 200 may include a nonwoven substrate layer or a film substrate layer that defines the first surface 202 and a second substrate layer defining the second surface 204, wherein the second substrate layer may include a nonwoven or a film.

The printed region 400 is generically represented herein as an oval shape on the first surface 202 of the substrate 200. It is to be appreciated that the printing station 302 can be configured to print a plurality of printed regions arranged along the machine direction MD and/or cross direction of the substrate 200. It is also to be appreciated that a single printed region 400 or a plurality of printed regions 400 may form a graphic. As used herein, the term "graphic" refers to images or designs that are constituted by a figure (e.g., a line(s)), a symbol or character, a color difference or transition of at least two colors, or the like. A graphic may include an aesthetic image or design that can provide certain benefit(s) when viewed. A graphic may be in the form of a photographic image. A graphic may also be in the form of a 1-dimensional (1-D) or 2-dimensional (2-D) bar code or a quick response (QR) bar code. A graphic design is determined by, for example, the color(s) used in the graphic (individual pure ink or spot colors as well as built process colors), the sizes of the entire graphic (or components of the graphic), the positions of the graphic (or components of the graphic), the movements of the graphic (or components of the graphic), the geometrical shapes of the graphic (or components of the graphics), the number of colors in the graphic, the variations of the color combinations in the graphic, the number of graphics printed, the disappearance of color(s) in the graphic, and the contents of text messages in the graphic.

It is to be appreciated that the printing station 302 may be configured in various ways and may include various types of printing accessories. For example, the printing station 302 may include a printer 306, which be configured in various ways. In some configurations, the printing station 302 may also include a corona treater, which may be positioned upstream of the printer 306. The corona treater may be configured to increase the surface energy of the surface of the substrate 200. For example, the corona treater may be configured to increase the surface energy of the surface to be printed to about 42 dynes/cm. In some configurations, the printer 306 may be in the form of a flexographic printer. In particular, a flexographic printer may utilize printing plates made of rubber or plastic with a slightly raised image thereon. The inked plates are rotated on a cylinder which transfers the image to the sheet. Some configurations may include a printer 306 in the form of a gravure printer. Gravure printing may utilize an image etched on the surface of a metal plate. The etched area is filled with ink and the plate is rotated on a cylinder that transfers the image to the substrate. In some configurations, printing devices such as disclosed in U.S. Patent Publication No. 2012/0222576 A1 may be used. In some configurations, the printer 306 may include various quantities of non-contact printheads arranged and/or configured in various ways to deposit inks onto the advancing substrate 200 to create printed regions 400. For example, in some embodiments, the printheads herein may be configured as inkjet printheads. Inkjet printing is a non-impact dot-matrix printing technology in which droplets of ink are jetted from a small orifice in the printhead directly to a specified position on a substrate to create a graphic. The inkjet printheads herein may be configured to perform different types of inkjet printing, such as for example, "drop-on-demand" and "continuous" inkjet printing.

With "continuous" inkjet printing processes, an ink is supplied under pressure to an inkjet nozzle and forced out through a small orifice. In some configurations, prior to passing out of the nozzle, the pressurized ink stream proceeds through a ceramic crystal, which is subjected to an electric current. The electric current causes a piezoelectric vibration equal to the frequency of an AC electric current. The vibration, in turn, generates the ink droplets from the unbroken ink stream. As such, the ink stream breaks up into a continuous series of drops which are equally spaced and of equal size. Surrounding the jet, at a point where the drops separate from the fluid stream in a charge electrode, a voltage is applied between the charge electrode and the drop stream. When the drops break off from the stream, each drop carries a charge proportional to the applied voltage at the instant at which it breaks off. By varying the charge electrode voltages at the same rate as drops are produced, it is possible to charge every drop to a predetermined level. The drop stream passes between two deflector plates which are maintained at a constant potential that deflects a drop towards one of the plates by an amount proportional to the charge carried. Drops that are uncharged are undeflected and collected into a gutter to be recycled to the ink nozzle. Those drops which are charged, and hence deflected, impinge on a substrate traveling at a high speed at right angles to the direction of drop deflection. By varying the charge on individual drops, a desired pattern can be printed. In some continuous inkjet printing configurations, the printer may utilize pulses of heat to create individual drops of ink, and then may use air to deflect the individual drops of ink.

With "drop-on-demand" inkjet printing processes, an ink is forced under pressure from the printhead through a relatively small orifice in the form of minute droplets by rapid pressure impulses. In some configurations, the orifice may have a diameter of about 0.0024 inches (5-50 microns). The rapid pressure impulses may be generated in the printhead by either expansion of a piezoelectric crystal vibrating at a high frequency or volatilization of a volatile composition (e.g. solvent, water, propellant) within the ink by rapid heating cycles. The piezoelectric crystal expansion causes the ink to pass through the orifice as minute droplets in proportion to the number of crystal vibrations. Thermal inkjet printers employ a heating element within the print head to volatilize a portion of the composition that propels the vast majority of fluid through the orifice nozzle to form droplets in proportion to the number of on-off cycles for the heating element. The ink is forced out of the nozzle when needed to print a spot on a substrate as part of a desired image. The minute droplets may also be energized to achieve an electrical charge and deflected as in the continuous inkjet printing process discussed above. Various inkjet printing processes are more particularly described in U.S. Pat. Nos. 3,465,350; 3,465,351; and 9,211,356.

Although the printing station 302 may include a single printhead, it is to be appreciated that printing stations 302 herein may be configured with more than one printhead arranged in the cross direction CD and/or machine direction MD. In some configurations, the printing stations 302 herein may include backup printheads, such as disclosed in U.S. Pat. No. 6,811,239. It is also to be appreciated that the printheads may be configured to print inks having the same colors or different colors. For example, a first ink may comprise a first color, and a second ink may comprise a second color different from the first color. In another example, a first ink may comprise a first color, and a second ink may comprise a second color that is the same as the first color. In addition, the printheads herein may be configured to perform single color, multi-color, halftone, and process printing.

"Halftone" or "halftoning" as used herein, sometimes referred to as "screening," is a printing technique that allows for less-than-full saturation of the primary colors. In halftoning, relatively small dots of each primary color are printed in a pattern small enough such that the average human observer perceives a single color. For example, magenta printed with a 20% halftone will appear to the average observer as the color pink. The reason for this is because, without wishing to be limited by theory, the average observer may perceive the tiny magenta dots and white paper between the dots as lighter, and less saturated, than the color of pure magenta ink. A "base color," as used herein, refers to a color that is used in the halftoning printing process as the foundation for creating additional colors. In some non-limiting embodiments, a base color is provided by a colored ink. Non-limiting examples of base colors may selected from the group consisting of: cyan, magenta, yellow, black, red, green, and blue-violet. "Black", as used herein, refers to a color and/or base color which absorbs wavelengths in the entire spectral region of from about 380 nm to about 740 nm. "Cyan", as used herein, refers to a color and/or base color which have a local maximum reflectance in the spectral region of from about 390 nm to about 570 nm. In some embodiments, the local maximum reflectance is between the local maximum reflectance of the blue or blue-violet and green local maxima. "Magenta", as used herein, refers to a color and/or base color which have a local maximum reflectance in the spectral region of from about 390 nm to about 490 nm and 621 nm to about 740 nm. "Yellow", as used herein, refers to a color and/or base color which have a local maximum reflectance in the spectral region of from about 571 nm to about 620 nm.

"Process Printing," as used herein, refers to the method of providing color prints using at least two of the primary of colors cyan, magenta, yellow and black. Each layer of color is added over a base substrate. In some embodiments, the base substrate is white or off-white in color. With the addition of each layer of color, certain amounts of light are absorbed (those of skill in the printing arts will understand that the inks actually "subtract" from the brightness of the white background), resulting in various colors. CMY (cyan, magenta, yellow) are used in combination to provide additional colors. Non-limiting examples of such colors are red, green, and blue. K (black) is used to provide alternate shades and pigments. One of skill in the art will appreciate that CMY may alternatively be used in combination to provide a black-type color.

An "ink" is a liquid containing coloring matter, for imparting a particular hue to a substrate. An ink may include dyes, pigments, organic pigments, inorganic pigments, and/or combinations thereof. It is also to be appreciated that the printing systems 300 herein may be configured to operate with various types of inks that dry when exposed to heat or ambient air for a given time. For example, the inks 304 herein may be configured as solvent or water based inks. In some examples, solvents and/or solvent blends may be used to achieve or help achieve desired physical properties, surface tension, viscosity, or specific gravity or a combination thereof. Example solvents for ink composition may include, without limitation, alcohols, acetates, ketones, glycol ethers, aromatic hydrocarbons, aliphatic naphthas, water, glycols, and combinations thereof. Alcohols may include ethyl alcohol, isopropyl alcohol, N-propyl alcohol, and blends thereof. Acetates may include ethyl acetate, N-propyl acetate, N-butyl acetate, isopropyl acetate, isobutyl acetate, butyl acetate, and blends thereof. Glycol ethers may include ethylene glycol monopropyl ether, ethylene glycol monobutyl ether, diethylene glycol monomethyl ether, diethylene glycol monopropyl ether, propylene glycol monomethyl ether, polyproylene glycol n-propyl ether, and blends thereof. Some solvents may include dipropylene glycol methyl ether, dipropylene glycol n-butyl ether, propolyene glycol, ethylene glycol, dipropylene glycol, and combinations or blends thereof.

In some configurations, a multi-stage printing system may be utilized. In some configurations, to improve ink rub-off resistance, ink compositions used herein may contain a wax. Such waxes may include a polyethylene wax emulsion. Addition of a wax to the ink composition may enhance rub resistance by setting up a barrier which inhibits the physical disruption of the ink film after application of the ink to the fibrous sheet. Based on weight percent solids of the total ink composition, addition ranges for the wax may be from about 0.5% solids to 10% solids. An example polyethylene wax emulsion is JONWAX 26 supplied by S.C. Johnson & Sons, Inc. of Racine, Wis.

In some configurations, the ink 304 may be compounded to be printed to meet select physical property ranges. While not wishing to be bound by theory, it is believed certain physical property ranges may affect some characteristics of the printed region 400. For example, the ink 304 may be configured with a surface tension to promote wetting of the substrate 200 by the ink 304. In another example, the ink 304 may be configured with a viscosity that promotes ink penetration into the substrate 200. In yet another example, the ink 304 may be configured with a specific gravity to promote wetting of the substrate 200 and thereby promoting ink penetration therein.

In some configurations, the ink 304 may have an ink composition that may have a relatively low surface tension compared to the surface tension of fibers that may make up the substrate 200, such as fibers in a nonwoven, or surfaces 202, 204 of the substrate, so as facilitate wetting by the ink composition. As such, the surface tension may provide desirable ink wetting of the substrate. In one nonlimiting example, the ink composition may have a surface tension as measured in dyne/cm at 25 degrees Celsius, which is numerically less than the surface tension of the fibers or surfaces making up the substrate 200, such as a nonwoven. In yet another example, the ink composition may have a surface tension as measured in dyne/cm at 25 degrees Celsius of less than 30.

In some configurations, the ink 304 may have an ink composition that may have a viscosity such that ink penetration occurs upon wetting the substrate 200. It is to be appreciated that various factors may influence ink penetration, such as for example, the ink's resistance to flow, thickness, and/or viscosity. In accordance with one example, the ink composition may have a viscosity in the range of 1 to 30 millipascal seconds. The viscosity measurement is done according to ASTM D 2196-99 Test Method A, where a UL adaptor is utilized and the measurements are made as outlined in ASTM D 2196-99, Test Method A at 25° C. and 60 rpm. Shake time and spindle selection are as indicated within the test method.

In some configurations, the ink 304 may have an ink composition that may have a specific gravity that also promotes wetting of the substrate, such as a nonwoven, and thereby promoting ink penetration therein. An example ink composition may have a specific gravity in the range of 0.830 to 1.050. The specific gravity is measured according to ASTM D 891-95 following Method A and determined at 25° C.

As previously mentioned and as shown in FIGS. 2-5, the printing system 300 includes the light source 308 that directs infrared light 310 onto the substrate 200 to define the illumination zone 312. It is to be appreciated that the infrared light 310 may have various wavelengths that may be used to dry the ink 304. In some configurations, the infrared light 310 may have wavelengths in the range of from about 700 nm to about 2,700 nm, or from about 800 nm to about 1,500 nm, reciting for each range every 10 nm increment therein.

Figure 5:
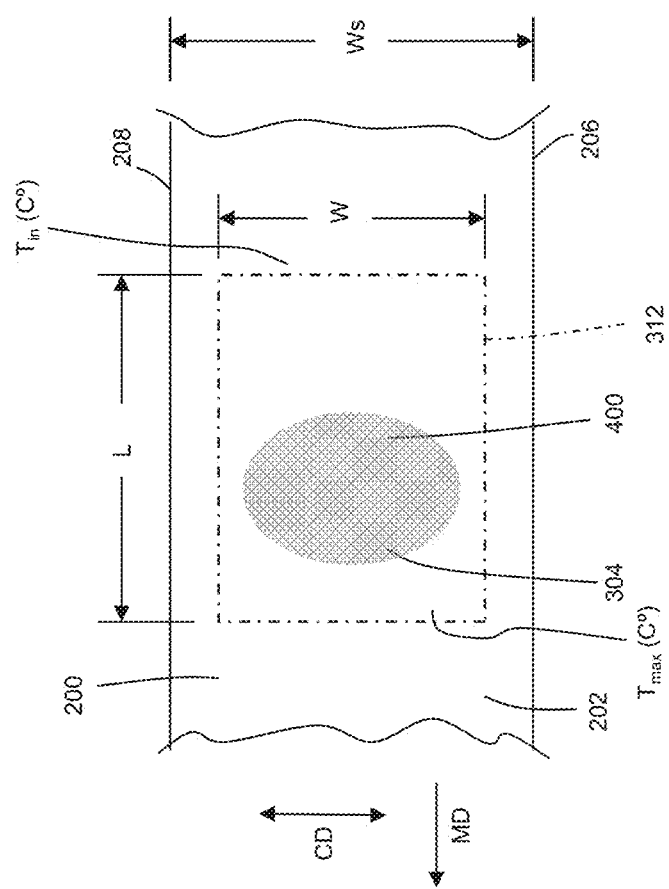
FIG. 5 is a top side view of the advancing substrate taken along the sectional line 5-5 of FIG. 3.

It is to be appreciated that the light source 308 shown in FIGS. 2-5 may be configured in various ways. For example, the light source 308 may include a window 309 that is positioned a distance D from the first surface 202 of the substrate 200. In some configurations, the distance D may be about 2 mm to about 50 mm. In some configurations, the distance D may be about 10 mm. In addition, the light source 308 may include one or more lamps that direct infrared light 310 toward the substrate 200 to define the illumination zone 312. In some configurations, the lamps may be configured as various types of infrared (IR) emitters, such as a hot wire in a glass tube. The light source 308 may also be configured to define illumination zones 312 having various different sizes and/or shapes. As shown in FIG. 5, the illumination zone 312 may extend for length L in the machine direction MD and may extend for a width W in the cross direction CD. In addition, the substrate 200 may define a width Ws in the cross direction CD between the first side edge 206 and the second side edge 208, and the width W of the illumination zone 312 may be greater than, equal to, or less than the width Ws of the substrate 200. It is also to be appreciated that the light source 308 may be configured such that light in the illumination zone 312 may have the same wavelength or different wavelengths along the length and/or width of the illumination zone 312. In addition, the light source 308 may be configured such that light in the illumination zone 312 may have the same intensity or different intensities along the length and/or width of the illumination zone 312. It should also be appreciated that the printing system 300 may include additional options associated with the drying of solvent or water based inks. For example, the printing system 300 may be configured to include a fan or a blower that may move air or some other gas relative to the printed region 400 to evaporate the components of the ink 304. In some configurations, air may be moved air across the first surface 202 of the substrate 200 or through the first surface 202 of the substrate 200 to help dry the ink 304. In addition, configurations may include other devices, such as a fan or blower configured to cool the light source 308.

As discussed above, during operation, the printing station 302 deposits ink 304 on the first surface 202 of the substrate 200 to define the printed region 400. As such, the printed region 400 includes an ink basis weight, IBW (gsm), that requires energy, Ec (J/m$^2$), to dry the ink 304. "Ink Basis Weight" (IBW) as used herein is the weight per unit area of a sample reported in grams per square meter (gsm) and is measured according to the Ink Basis Weight Test Method described herein. In the illumination zone 312, the infrared light 310 comprises an intensity I (W/m$^2$) at the first surface 202 of the substrate 200. Thus, the ink 304 may need to be subjected to the intensity I (W/m$^2$) for a period of time so as to reach the energy level Ec (W/m$^2$). As discussed above, the substrate 200 advances in the machine direction MD at a speed S (m/s), and the illumination zone 312 extends in the machine direction for a length (L). In turn, ink 304 of the printed region 400 advances through the illumination zone 312 at speed S (m/s), and thus, the time to advance through the illumination zone 312 is equal to: L (m)/S (m/s). Thus, the intensity and time needed to dry ink 304 advancing through the illumination zone 312 should be equal to or greater than the energy required to dry the ink 304 applied to the substrate 200 with a particular ink basis weight, and may be expressed by the following equation:

$$[I\ (W/m^2) \times L\ (m)/S\ (m/s)] \geq Ec\ (J/m^2)].$$

It is to be appreciated that the printed regions 400 herein may have various ink basis weights. For example, in some configurations, the printed region 400 may have an ink basis weight of at least about 0.10 gsm, or at least about 1.0 gsm, or at least about 1.5 gsm, or from about 1 gsm to about 7 gsm, or about 1.5 gsm to about 5.5 gsm, or about 6 gsm or less. It is also to be appreciated that the printed regions 400 may have various print resolutions. For example, the printed region 400 may have a print resolution of at least about 64 dpi, or at least about 100 dpi, or from about 64 dpi to about 1200 dpi, or from about 200 to about 400 dpi, or about 400 dpi or less, reciting for each range every 1 dpi increments therein and all ranges formed therein or thereby in the cross machine direction of the substrate 200, which in some configurations corresponds to the lateral direction of the substrate. In some examples, the printed region 400 may have a print resolution of at least about 10 dpi, or about 6000 dpi or less, or about 1500 dpi or less, or about 100 dpi or less, or from about 10 dpi to about 6000 dpi, reciting for each range every 1 dpi increments therein and all ranges formed therein or thereby in the machine direction of the substrate 200, which in some configurations corresponds to the longitudinal direction of the substrate 200. The ink 304 may also comprise a colorant. In some configurations, the ink 304 comprises cyan, magenta, yellow, black, or combinations thereof. The ink 304 may also be disposed on at least 1%, or at least, 5%, or at least 10%, or at least 20%, or at least 25%, or from about 10% to about 90% of the surface based on the total area of the surface as determined by the Percent Printed Color Area Test Method herein.

As previously discussed, the substrate 200 absorbs energy used to the dry the ink 304 in the illumination zone 312, which in turn, may cause the temperature of substrate 200 to increase. For example, in some configurations where printing is performed online during an article assembly process, ink 304 may be required to advance past the infrared light 310 in the illumination zone 312 at a relatively high rate of speed S (m/s). As such, the time during which ink 304 is exposed to infrared light 310 may be relatively short. As discussed above, in order to dry the ink 304 in a relatively short period of time, the intensity of the infrared light 310 may need to be increased to relatively high levels. However, if the intensity is too high over a period of time, the heat energy created in the substrate 200 from the infrared light 310 may destroy and/or damage the advancing substrate 200.

To help prevent damage to the substrate 200 during the drying process, the printing system 300 may be configured to maintain the temperature of the substrate 200 at or below an onset temperature, $T_{onset}$ (C°). As used herein, the onset temperature, $T_{onset}$ (C°), of a substrate is determined by the Differential Scanning calorimetry Test Method herein. In turn, the printing system 300 may be configured such that the infrared light 310 heats the substrate 200 from an initial temperature $T_{in}$ (C°) entering the illumination zone 312 to a maximum temperature $T_{max}$ (C°), wherein $T_{max}$ (C°)≤ $T_{onset}$ (C°) in the illumination zone 312, such as schematically represented in FIG. 5. In some configurations, the maximum temperature $T_{max}$ (C°) of the substrate 200 in the illumination zone 312 may be maintained below the onset temperature, $T_{onset}$ (C°) by controlling the speed S (m/s) at which the printed region 400 advances through the illumination zone at a speed S (m/s) and/or by controlling the length L (m) and/or width W (m) of the illumination zone 312 so as to control the time at which the ink 304 is exposed to the infrared light 310 having an intensity I (W/m²) in the illumination zone 312. In addition, the intensity I (W/m²) infrared light 310 in the illumination zone 312 may be controlled. In some configurations, the light source 308 may operate to ramp up and ramp down the intensity I (W/m²) in the illumination zone 312 during production line start up and shutdown, respectively, to help protect the substrate 200 while advancing relatively slowly through the illumination zone 312.

In some configurations, the printing system 300 may include a cooling apparatus that removes heat energy from the substrate 200 before, during, and/or after the printed region 400 advances through the illumination zone 312. It is to be appreciated that the printing systems 300 herein may include one or more cooling apparatuses that may be configured in various ways. For example, the cooling apparatus may include a heat exchanger, such as a heat sink. In some examples, the cooling apparatus may include a device, such as a fan or blower, moves air or other gas along the first surface 202 and/or second surface 204 the substrate 200 to remove heat energy from the substrate 200 with convection. It is to be appreciated that the cooling apparatus may be configured with components that are in close proximity with or in contact with the first surface 202 and/or the second surface 204 of the substrate 200. Example configurations of such cooling apparatuses are disclosed in U.S. Provisional Patent Application No. 62/467,995, entitled "Method and Apparatus for Curing Inks Printed on Heat Sensitive Absorbent Article Components," filed on Mar. 7, 2017, which is incorporated by reference herein.

When printing on fibrous substrates, such as nonwovens, the printed ink 304 may penetrate into the substrate 200. In some instances, some of the ink 304 may flow or migrate entirely through the substrate 200 from the first surface 202 to the second surface 204. In addition, a portion of the infrared light 310 traveling from the light source 308 may also travel through substrate 200 and away from the second surface 204 of the substrate 200. As such, the printing systems 300 herein may include a reflective device, such as a mirror, that reflects infrared light 310 traveling from the second surface 204 of the substrate 200 back toward the second surface 204 of the substrate 200 to dry the ink 304 that may have flowed or migrated entirely through the substrate 200 from the first surface 202 to the second surface 204. In some configurations, the cooling apparatus may be configured to reflect the infrared light 310 as described above. Example configurations of reflective devices are disclosed in U.S. Provisional Patent Application No. 62/467,976, entitled "Method and Apparatus for Curing Inks Printed on Fibrous Absorbent Article Components," filed on Mar. 7, 2017, which is incorporated by reference herein.

It is to be appreciated that the printing system 300 herein may also include various additional features. For example, as previously mentioned, the printing system 300 may be configured to print off-line or interact with and/or be configured as a unit operation of a converting line. In some configurations of the printing system 300, the printer 306, the light source 308, and/or the metering device 314 may be arranged adjacent the advancing substrate 200, and the printer 306, the light source 308, and/or the metering device 314 may interface and communicate with a controller 324. The controller 324 may be adapted to control the operation of the printer, light source, metering device, and/or may allow an operator to manually program the type of graphics to be printed. For example, the printing system 300 may be configured with various features, such as available on the Prosper S20 Ink Jet Printer available from Kodak. In some configurations, the printing system 300 may be configured to interface with other computerized systems and/or networks that may automatically program or command the printing system to print various graphics based on various input, such as sales orders from customers. It is to be appreciated that the controller 324 may be configured in various ways. For example, the controller 324 may be in the form of a personal computer (PC) or a central processing unit (CPU). The controller 324 may also be configured to monitor and affect various operations on a converting line. For example, the controller 324 may send various types of control commands to the converting line based on communications with sensors adjacent the converting line.

It is to be appreciated that the controller 324 may also be configured to communicate with one or more computer systems, such as for example, a programmable logic controller (PLC) and/or personal computer (PC) running software and adapted to communicate on an EthernetIP network. Some embodiments may utilize industrial programmable controllers such as the Siemens S7 series, Rockwell ControlLogix, SLC or PLC 5 series, or Mitsubishi Q series. The aforementioned embodiments may use a personal computer or server running a control algorithm such as Rockwell SoftLogix or National Instruments Labview or may be any other device capable of receiving inputs from sensors, performing calculations based on such inputs and generating control actions through servomotor controls, electrical actuators or electro-pneumatic, electrohydraulic, and other actuators. In some configurations, process and product data may be stored directly in the aforementioned computer systems or may be located in a separate data historian. In some embodiments, the historian is a simple data table in the controller. In other embodiments, the historian may be a relational or simple database. Common historian applications include Rockwell Automation Factory Talk Historian, General Electric Proficy Historian, OSI PI, or any custom historian that may be configured from Oracle, SQL or any of a number of database applications. It is also to be appreciated that the controller 324 may be configured to communicate with various types of controllers and inspection sensors configured in various ways and with various algorithms to provide various types of data and perform various functions, for example, such as disclosed in U.S. Pat. Nos. 5,286,543; 5,359,525; 6,801,828; 6,820,022; 7,123,981; 8,145,343; 8,145,344; and 8,244,393; and European Patent No. EP 1528907 B1, all of which are incorporated by reference herein.

As shown in FIGS. 2-4, the printer 306, light source 308, and/or metering device 314 may be in communication with the controller 324 through a communication network 326. As such, it is to be appreciated that the controller 324 may be physically located near the advancing substrate 200, printing station 302, the light source 308, and/or metering device 314 and/or may be located at another location and in communication with the printer 306, the light source 308, and/or the metering device 314 via a wired and/or wireless network 326. In some embodiments, the communication network 326 is configured as a non-deterministic communication network, such as for example, Ethernet or Ethernet IP (industrial protocol) communication network.

It is also to be appreciated that the printing systems 300 herein may be configured to print printed regions 400 at desired print resolutions on a substrate 200, wherein the printed regions may form graphics G, such as shown in FIG. 1 and discussed above with reference to absorbent articles assembled with various components that may be printed off-line, before assembly, or on-line, as part of the assembly process. Thus, in the context of the previous discussion, the printing system 300 herein may be used to print substrates and components of an absorbent article 100, either off-line or on-line. For example, the printing system 300 herein may be utilized to print printed regions on a sanitary napkin to form graphics on any of the topsheet 114; secondary topsheet 119, backsheet 116; wings 120; and/or absorbent core 118 before or during the manufacture of an absorbent article 100. In other examples, the printing system 300 herein may be utilized to print printed regions on a diaper to form graphics on any of a topsheet; backsheet; absorbent core; leg cuffs; waist features; side panels; connection zones; fastening elements; and/or belts.

Ink Basis Weight Test Method

Remove the printed substrate from the product without damaging the printed substrate.

Punch out a material swatch with a known area (e.g. 1 cm^2 punch) of printed material where you would like to determine the ink basis weight.

Punch out the same printed area on 100 different products. Combine all 100 material swatches and weigh. Record the total weight in grams to 2 decimal places of the 100 printed material swatches.

Punch out a material swatch with a known area (e.g. 1 cm^2 punch) of the same substrate as the printed material, but this time in an area without any ink on it.

Punch out the same non-printed area on 100 different products.

Combine all 100 material swatches and weigh. Record the total weight in grams to 2 decimal places of the 100 non-printed material swatches.

Use the equation below to calculate the ink basis weight for the given printed area.

$$\text{Ink Basis Weight} = \frac{\text{Printed Material Mass}}{\text{Printed Punch Area} \times \text{\# of Printed Repeats}} - \frac{\text{Non-Printed Material Mass}}{\text{Non-Printed Punch Area} \times \text{\# of Non-Printed Repeats}}$$

Percent Printed Color Area Test Method

Percent Printed Color Area is used to determine the amount of printed color coverage on a component layer of an absorbent article images acquired using a flatbed scanner. The scanner is capable of scanning in reflectance mode at a resolution of 150 dpi and 24 bit color (a suitable scanner is an Epson Perfection V750 Pro from Epson America Inc., Long Beach Calif. or equivalent). The scanner is interfaced with a computer running an image analysis program (a suitable program is ImageJ v. 1.50 or equivalent, National Institute of Health, USA). The specimen images are distance calibrated against an acquired image of a ruler certified by NIST. The resulting image is then analyzed using the image analysis program to identify the boundaries of the printed color regions and calculate the percent printed color area.

Remove the printed substrate of interest from an absorbent article using cryogenic spray (such as Cyto-Freeze, Control Company, Houston Tex.) or other means as needed to separate the substrate from other components of the article and avoid any longitudinal and lateral distortion of the specimen. Five replicates of this specimen layer, obtained from five substantially similar absorbent articles, are prepared for analysis. Precondition the specimens at about 23° C.±2° C. and about 50%±2% relative humidity for 2 hours prior to testing.

Place the ruler on the center of the scanner bed, oriented parallel to the sides of the scanner glass, and close the lid. Acquire a calibration image of the ruler in reflectance mode at a resolution of 150 dpi (approximately 5.9 pixels per mm) and 24 bit color. Save the calibration image as an uncompressed TIFF format file. Lift the lid and remove the ruler. After obtaining the calibration image, all specimens are scanned under the same conditions and measured based on the same calibration file. Next, place the specimen onto the center of the scanner bed, lying flat, with the color printed facing surface of the specimen facing the scanner's glass surface. Cover the specimen with a white background (in this test method white is defined as having L*>94, −2<a*<2, and −2<b*<2 based on the standard CIE L*a*b* color space) and close the lid. Acquire and save a scanned image of the specimen layer. If the size of the specimen layer exceeds the available scanning area, obtain multiple scans covering the entire specimen layer and digitally stitch them together into a single image for analysis. Scan the remaining four replicates in like fashion.

Open the calibration image file in the image analysis program and perform a linear distance calibration using the imaged ruler. This distance calibration scale will be applied to all subsequent specimen images prior to analysis. Open a specimen image in the image analysis program and set the distance scale. Using the image analysis program, identify and define the boundaries of any printed color regions in the image of the specimen layer. Identification of color region boundaries should be performed with the intent of defining them as they would be discerned by a human viewer under standard lighting conditions with the unaided eye if the layer were being viewed face on in a flat configuration at approximately an arm's length distance. For example, intra-dot spaces commonly associated with ink-jet printing are included within that ink region, because they are perceived as part of that printed region by a typical viewer without magnification.

Calculate the area of each of the individual printed color regions within the image to the nearest 0.1 mm². Calculate the total area of printed color by summing up the areas of the individual printed color regions. Divide the total area of the printed color regions by the area of the entire specimen layer and multiply by 100. Record this value as the printed color percent area to the nearest 0.1%. In like fashion, analyze the remaining four specimen images. Calculate and report the average printed color percent area to the nearest 0.1% for the five replicates.

Differential Scanning Calorimetry Test Method

The Differential Scanning calorimetry measurement is run according to ASTM 3418-15 with the following specifications: All testing is performed in a room controlled at 23° C.±3° C. and 50%±2% relative humidity. Condition all samples for two hours prior to specimen preparation and testing. Prepare three (3) replicate sealed test specimens by cutting them from a non-printed area of the nonwoven, film, laminate, or substrate adjunct to the printed area to a weight of 5-10 mg, but not exceeding a circular area with 2.5 mm in diameter. Run the method as specified in ASTM 3418-15 with a ramp of 20° C./min up to 400° C. Record the $T_{eim}$=melting extrapolated onset temperature in ° C. for the first heat for each of the three test specimens Average the three $T_{eim}$ values and report as the onset temperature, $T_{onset}$ (C°), to the nearest degree C.

This application claims the benefit of U.S. Provisional Application No. 62/507,253, filed on May 17, 2017, the entirety of which is incorporated by reference herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for printing, the method comprising the steps of:
   providing a continuous substrate extending in a machine direction, the continuous substrate comprising a first surface and an opposing second surface and defining a width in a cross direction;
   directing infrared light from a light source onto the first surface of the substrate to define an illumination zone extending for a length, L (m), in the machine direction on the first surface of the substrate;
   advancing the substrate under a printhead;
   ejecting ink from the printhead onto the first surface of the substrate to define a printed region;
   advancing the substrate and the printed region from the printhead to a metering device comprising a vacuum conveyor;
   advancing the printed region from the vacuum conveyor through the illumination zone;
   drying the ink advancing through the illumination zone with infrared light traveling from the light source.

2. The method of claim 1, wherein the infrared light comprises an intensity I (W/m²) at the first surface of the substrate in the illumination zone, and wherein the printed region comprises an ink basis weight, IBW (gsm), that requires energy, Ec (J/m²), to dry the ink; and further comprising the step of:
   advancing the printed region through the illumination zone at a speed, S (m/s), such that $$[I\ (W/m^2) \times L\ (m)/S\ (m/s)] \geq Ec\ (J/m^2)].$$

3. The method of claim 1, wherein the printhead comprises a maximum firing frequency equal to or greater than about 400 kHz.

4. The method of claim 1, wherein the printed region comprises:
   a first print resolution extending in the machine direction of equal to less than about 300 dots per inch; and
   a second print resolution extending in the cross direction of equal to less than about 600 dots per inch.

5. The method of claim 1, wherein the substrate comprises an onset temperature $T_{onset}$ (C°) and further comprising the step of advancing the printed region through the illumination zone at a speed, S (m/s), such that the infrared light heats the substrate from an initial temperature $T_{in}$ (C°) entering the illumination zone to a maximum temperature $T_{max}$ (C°), wherein $T_{max}$ (C°)≤$T_{onset}$ (C°) in the illumination zone.

6. An apparatus for printing on a continuous substrate extending in a machine direction, the continuous substrate comprising a first surface and an opposing second surface and defining a width in a cross direction, the apparatus comprising:
   a supply of water based ink;
   a printing station positioned to deposit ink from the supply onto the first surface of the substrate;
   an ink dryer comprising a light source positioned to direct infrared light toward the first surface of the substrate at a location downstream in the machine direction from the printing station, wherein heat from the ink dryer causes changes in the modulus of elasticity of the substrate; and
   a means for eliminating phase shifting caused by changes in the modulus of elasticity of the substrate, the means for eliminating phase shifting is positioned between the printing station and the ink dryer.

7. The apparatus of claim 6, wherein means for eliminating phase shifting comprises a vacuum conveyor.

* * * * *